US010912512B2

(12) United States Patent
Moradi et al.

(10) Patent No.: US 10,912,512 B2
(45) Date of Patent: Feb. 9, 2021

(54) SYSTEM AND METHOD FOR MUSCLE MOVEMENTS DETECTION

(71) Applicants: Ali Moradi, Mashhad (IR); Ehsan Vahedi, Mashhad (IR); Saeed Kermani, Mashhad (IR); Mohammad Hosein Ebrahimzadeh, Mashhad (IR); Alireza Akbarzadeh Tootoonchi, Mashhad (IR); Saeed Bahrami Moqadam, Mashhad (IR); Hamed Jafarzadeh, Mashhad (IR); Seyedpouya Pishbin, Mashhad (IR)

(72) Inventors: Ali Moradi, Mashhad (IR); Ehsan Vahedi, Mashhad (IR); Saeed Kermani, Mashhad (IR); Mohammad Hosein Ebrahimzadeh, Mashhad (IR); Alireza Akbarzadeh Tootoonchi, Mashhad (IR); Saeed Bahrami Moqadam, Mashhad (IR); Hamed Jafarzadeh, Mashhad (IR); Seyedpouya Pishbin, Mashhad (IR)

(*) Notice: Subject to any disclaimer, the term of this patent is extended or adjusted under 35 U.S.C. 154(b) by 259 days.

(21) Appl. No.: 16/027,339

(22) Filed: Jul. 4, 2018

(65) Prior Publication Data
US 2019/0000380 A1    Jan. 3, 2019

Related U.S. Application Data

(60) Provisional application No. 62/528,459, filed on Jul. 4, 2017.

(51) Int. Cl.
*A61F 2/68*    (2006.01)
*A61B 5/00*    (2006.01)
(Continued)

(52) U.S. Cl.
CPC ............ *A61B 5/4851* (2013.01); *A61B 5/064* (2013.01); *A61B 5/1107* (2013.01);
(Continued)

(58) Field of Classification Search
CPC ....... A61B 5/4815; A61B 5/64; A61B 5/1107; A61B 5/1127; A61B 5/4519; A61B 5/587;
(Continued)

(56) References Cited

U.S. PATENT DOCUMENTS 8,145,318 B2    3/2012    Van Herk
9,299,248 B2 *  3/2016    Lake ..................... G08C 17/02
(Continued)

FOREIGN PATENT DOCUMENTS

JP    2010051682 A    3/2010

OTHER PUBLICATIONS

Keisuke Shima and Toshio Tsuji, An MMG-based Human-Assisting Manipulator Using Acceleration Sensors, Proceedings of the 2009 IEEE International Conference on Systems, Man, and Cybernetics, San Antonio, TX, USA, pp. 2433-2438.
(Continued)

*Primary Examiner* — Suba Ganesan
*Assistant Examiner* — Aren Patel
(74) *Attorney, Agent, or Firm* — Bajwa IP Law Firm; Haris Zaheer Bajwa

(57) ABSTRACT

Disclosed herein a system and a method to detect an amputee's hand muscles movements for controlling an artificial limb prosthesis. The system may comprise a plurality of passive tag positions and wearable band with a plurality of on-board position readers. The plurality of on-board position readers may be configured to capture data associated with a first plurality of passive tags positions at a first moment, and capture data associated with a second plurality
(Continued)

of passive tags positions at a second moment. The system may further include one or more processors configured to detect at least one of the muscle contraction, the muscle relaxation, and the muscle inactivity based on the data captured at the first moment and at the second moment, and thereby control the artificial hand prosthesis movements responsive to detection at least one of the muscle contraction, the muscle relaxation, and the muscle inactivity.

20 Claims, 6 Drawing Sheets

(51) Int. Cl.
| | | |
|---|---|---|
| A61B 5/11 | (2006.01) | |
| A61B 90/98 | (2016.01) | |
| A61B 5/06 | (2006.01) | |
| A61F 2/58 | (2006.01) | |
| A61F 2/76 | (2006.01) | |
| A61F 2/72 | (2006.01) | |
| A61F 2/78 | (2006.01) | |
| A61B 90/00 | (2016.01) | |
| A61F 2/70 | (2006.01) | |

(52) U.S. Cl.
CPC .......... *A61B 5/1127* (2013.01); *A61B 5/4519* (2013.01); *A61B 90/98* (2016.02); *A61F 2/583* (2013.01); *A61F 2/585* (2013.01); *A61F 2/72* (2013.01); *A61F 2/76* (2013.01); *A61F 2/7812* (2013.01); *A61B 5/6824* (2013.01); *A61B 2090/397* (2016.02); *A61B 2090/3908* (2016.02); *A61B 2090/3925* (2016.02); *A61B 2090/3954* (2016.02); *A61B 2090/3991* (2016.02); *A61B 2562/046* (2013.01); *A61B 2562/066* (2013.01); *A61F 2002/587* (2013.01); *A61F 2002/6863* (2013.01); *A61F 2002/701* (2013.01); *A61F 2002/704* (2013.01); *A61F 2002/762* (2013.01); *A61F 2002/7615* (2013.01); *A61F 2002/7837* (2013.01)

(58) Field of Classification Search
CPC .... A61B 2090/3908; A61B 2090/3925; A61B 2090/3954; A61B 2090/397; A61B 2090/3991; A61F 2/583; A61F 2/585; A61F 2/68; A61F 2/72; A61F 2/76; A61F 2/7812; A61F 2002/587; A61F 2002/6863; A61F 2002/701; A61F 2002/704; A61F 2002/7165; A61F 2002/762; A61F 2002/7837
USPC .......................................................... 923/25
See application file for complete search history.

(56) References Cited

U.S. PATENT DOCUMENTS

| | | | |
|---|---|---|---|
| 2013/0172691 A1* | 7/2013 | Tran ......................... | A61B 8/06 600/301 |
| 2014/0067083 A1* | 3/2014 | Wenstrand .............. | A61F 2/583 623/24 |
| 2016/0262687 A1* | 9/2016 | Vaidyanathan ...... | A61B 5/1123 |
| 2016/0361820 A1* | 12/2016 | Davis ..................... | A61B 5/225 |
| 2018/0020973 A1* | 1/2018 | Hurley ..................... | A61F 2/76 623/24 |
| 2018/0098864 A1* | 4/2018 | Auberger .................. | A61F 2/68 |

OTHER PUBLICATIONS

L.P.J. Kenney, Dimensional change in muscle as a control signal for powered upper limb prostheses, Medical Engineering & Physics 21 (1999) 589-597.

Nan Bu, Measuring Muscle Movements for Human Interfaces using a Flexible Piezoelectric Thin Film Sensor, surgical technique, 30th Annual International IEEE EMBS Conference, Vancouver, British Columbia, Canada, Aug. 20-24, 2008, pp. 112-116.

* cited by examiner

SYSTEM AND METHOD FOR MUSCLE MOVEMENTS DETECTION

CROSS-REFERENCE TO RELATED APPLICATION

This application claims the benefit of priority from U.S. Provisional Patent Application Ser. No. 62/528,459, filed on Jul. 4, 2017, and entitled "A CONTROL SYSTEM FOR DETECTING MUSCLE MOVEMENTS" which is incorporated herein by reference in its entirety.

TECHNICAL FIELD

The present disclosure generally relates to muscle movements detection systems and methods, and particularly to a system and a method for detecting muscle movements by utilizing implanted passive tags.

BACKGROUND

For moving any joint in the body, a signal from brain is needed. In order to move a joint, brain may send a voluntary signal to respective peripheral nerve and, consequently, the nerve may stimulate the specific muscle so that the muscle is contracted and thereby pulling the respective tendon to flex the related joint.

For purpose of reference, it should be understood that any interruption in above cycle may abort the movement intention. For example, limb amputation or nerve damage may substantially abort the movement intention. Limb amputation or nerve damage may occur due to diseases such as arteriosclerosis, diabetes and Buerger disease, injuries caused by cutting edges, car or industrial accidents, infections, tumors, congenital deformities, or the like.

The number of disabled persons dealing with congenital or acquired deformities is increasing every year. Accordingly, their rehabilitation and ability to have enhanced functionality for disabled persons impacted by limb amputation is considered as a great issue.

Most of disabled persons impacted by limb amputation rehabilitate by wearing a prosthetic hand, a prosthetic leg, or an assistive device and training. If such rehabilitation tools are used, a user may not be able to replicate touching senses or conduct some complicated tasks such as writing, grasping, and manipulating a grasped object. In addition, if an amputee is impacted by serious limb amputation or nerve cutting, wearing and controlling such an assist device may be substantially impossible.

In relation to existing nerve signal detection and stimulation approaches, techniques such as a depth type, a planar type, a sieve type and a cuff type are used. The planar type (which is also called MicroElectrode Array (MEA)) is directed to measuring a nerve signal by means of nerve cell cultivation. However, since the planar type is generally utilized for studying a method for analyzing signals of a nerve system or a method for inputting information to the nerve system, it is not suitable to apply the planar type to a technique of connecting a nerve system and an artificial device.

The depth type represents a method of directly inserting an electrode into a nerve tissue and using the electrode. The electrode collects electric signals from surrounding nerves. However, an insertion type electrode may cause necrosis or accumulations of surrounding cells due to long time use, which may prevent active signals of nerves from being stably measured. In other words, due to the feature of nerves which are composed of several bundle type efferent axons, there is a limit in distinguishing signals accurately.

The sieve type, also called nerve-generating type, generally uses regenerating ability of nerves where a sieve-shaped electrode is placed between cut nerves so that the efferent axons of the nerve cells are regenerated while passing between the sieve-shaped electrodes. By doing so, a nerve signal may be measured. However, the sieve electrode may be used only when being located between cut nerves, namely only when nerves are alive at both terminals, and so the scope of its application is limited.

The cuff type is directed to measuring a nerve signal by surrounding nerves directly. Since the cuff type measures a nerve signal from outside of nerves surrounded by an insulator, it is difficult to measure an accurate signal and separate afferent and/or efferent signals.

However, existing artificial prosthetic hands or prosthetic feet are able to determine the intent of a behavior by means of body power or surface electromyogram but are, generally, disregarded by patients due to low recognition rate and malfunctions. On the other hand, the existing systems and methods described above have various other limitations in detecting nerve signals of cut peripheral nerves composed of bundle type efferent axons and freely controlling a prosthetic limb through stimulation. There is, therefore, also a need for muscle movements detection and prosthetic limb control systems and methods that improve the accuracy and/or efficiency of distinguishing an amputee's intention for moving a part of an amputated limb.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

According to one or more exemplary embodiments, the present disclosure describes a system to detect an amputee's hand muscles movements for controlling an artificial hand prosthesis. The system may comprise a plurality of passive tags, a wearable band, and one or more processors.

In an exemplary embodiment, each passive tag of the plurality of passive tags may be fixedly embedded into a respective muscle of the plurality of muscles in a configuration such that is responsive to the muscle being contracted or relaxed, the passive tag thereby moving.

In an exemplary embodiment, the wearable band may include a plurality of on-board position readers. Furthermore, the plurality of on-board position readers may be configured to capture data associated with a first plurality of passive tags positions at a first moment, and also configured to capture data associated with a second plurality of passive tags positions at a second moment. In an exemplary embodiment, the plurality of on-board position readers may comprise 30 on-board position readers that are arranged in a 5 by 6 matrix arrangement. And also a subset of the plurality of on-board position readers may be arranged circumferentially around the wearable band.

In an exemplary embodiment, the processors may be configured to detect at least one of the muscle contraction, the muscle relaxation, and the muscle inactivity based on the data captured at the first moment and the second moment, and also may be configured to control the artificial hand prosthesis movements responsive to detection of the muscle contraction, the muscle relaxation, and the muscle inactivity.

In an exemplary embodiment, the plurality of passive tags may comprise a plurality of RFID tags coated with a biocompatible silicon or any other biocompatible material. And also each passive tag of the plurality of passive tags may be sutured or otherwise may be fixed to a superficial part of the respective muscle close to a skin surface. Furthermore, in an exemplary embodiment, each passive tag of the plurality of passive tags may be sutured to a part of the respective muscle close to a muscle-tendon junction. In an exemplary embodiment, the plurality of passive tags may include a first passive tag and a second passive tag such that a distance between the first passive tag and the second passive tag is larger than 2 centimeters.

In an exemplary embodiment, one or more processors may be configured to detect at least one of the muscle contraction, the muscle relaxation, and the muscle inactivity based on the data captured at the first moment and the second moment by comparing the x-coordinate and y-coordinate as well as z-coordinate of each passive tag position of the first plurality of passive tags positions with the respective coordinates of the respective passive tag position of the second plurality of passive tags positions.

Furthermore, one or more processors may be configured to detect at least one of the muscle contraction, the muscle relaxation, and the muscle inactivity based on the data captured at the first moment and the second moment by comparing the y-coordinate of each passive tag position of the first plurality of passive tags positions with the y-coordinate of the respective passive tag position of the second plurality of passive tags positions and also by comparing the z-coordinate of each passive tag position of the first plurality of passive tags positions with the z-coordinate of the respective passive tag position of the second plurality of passive tags positions.

In an exemplary embodiment, one or more processors may be configured to detect the muscle contraction responsive to a value of the x-coordinate of the first associated tag position be smaller than a value of the x-coordinate of the second associated tag position, detect the muscle relaxation responsive to a value of the x-coordinate of the first associated tag position be larger than a value of the x-coordinate of the second associated tag position, and, detect the muscle inactivity responsive to a value of the x-coordinate of the first associated tag position be equal to a value of the x-coordinate of the second associated tag position.

According to one or more implementations of the present disclosure, a method may be performed by fixedly embedding a passive tag of a plurality of passive tags into a muscle of a plurality of muscles and capturing data associated with a first plurality of passive tags positions at a first moment by a plurality of on-board position readers attached to a wearable band. In an exemplary embodiment, the plurality of passive tags may be embedded in muscles of a plurality of muscles and a respective passive tag of the plurality of passive tags may be fixedly embedded into a respective muscle of the plurality of muscles in a configuration that responsive to the muscle being contracted or relaxed, the passive tag thereby moving.

In an exemplary embodiment, the disclosed method may further include capturing data associated with a second plurality of passive tags positions at a second moment by the plurality of on-board position readers and detecting at least one of the muscle contraction, the muscle relaxation, and the muscle inactivity based on the data captured at the first moment and the second moment by a processor and controlling the artificial hand prosthesis movements responsive to detection of the muscle contraction, the muscle relaxation, and the muscle inactivity.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
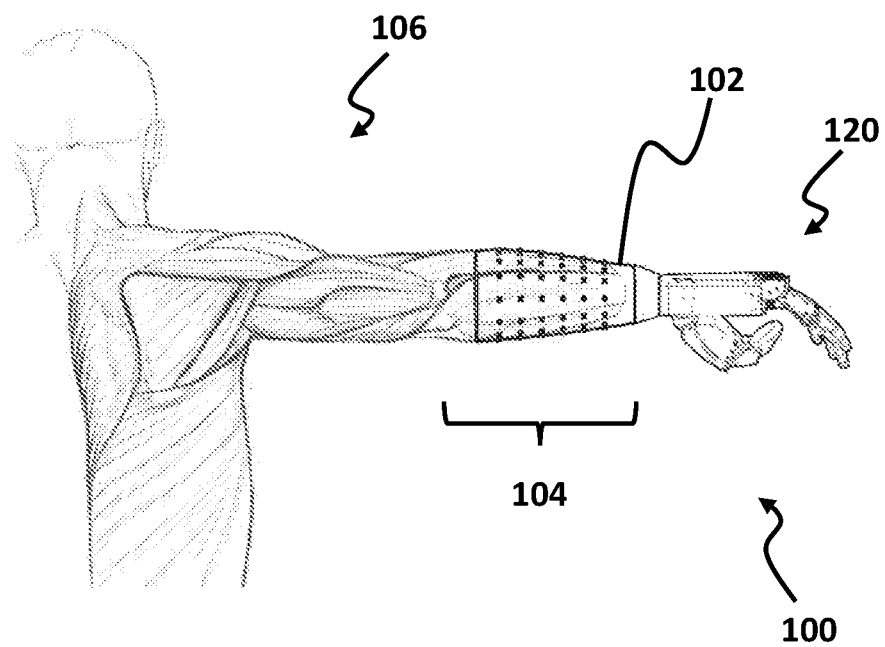
FIG. 1A illustrates a muscle movement detection system worn on a remainder part of an amputated hand, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

As noted above, detection of muscles movements is becoming an important feature in medical diagnosis, treatment, and rehabilitation. One application of detecting muscles movements may be to identify an amputee's intention for moving the amputated part of the body. In exemplary embodiments, this detection may help manipulating an artificial prosthesis. As a solution, recording of muscle activity may be, generally, used to generate control signals for human-assisting manipulators prosthetic devices. Electromyography (hereinafter referred to EMG) signals, measured at the skin surface, are able to provide some information about neuromuscular activities. Surface EMG has been extensively used in a number of researches to detect human movements or intentions of movement with a pattern classification process. Up until now, numerous EMG-based human interface applications have been proposed. It has been suggested, however, that the amplitude of EMG is substantially low, and signals measured are usually affected by artifacts and noises and long-term usage may cause fatigue or stress in muscles. Moreover, electrodes are needed for sensing EMG signals. This approach also suffers from several drawbacks including, but are not limited to, the fact that conductive cream or gel is messy and often causes discomfort to users and changes of the skin-electrode impedance may affect signal-to-noise ratio. Then, many conscious efforts are required to achieve a more reliable control signal for human interfaces.

On the other hand, during contraction and/or relaxation of a muscle, the muscle's cross-sectional area may increase or otherwise may decrease. This morphological change may be utilized to detect the functional and contractile state of muscles and consequently may be used as a control signal for manipulating an artificial prosthesis. As will be discussed herein, systems directed to detecting muscles movements, for example, hand muscles movements by detecting a morphological change in hand muscles, are disclosed.

In some embodiments of the present disclosure, the disclosed system may comprise a wearable band with a plurality of readers, a plurality of tags, and a controller. In an exemplary embodiment, each of the plurality of tags may be embedded or otherwise attached to a respective muscle of the forearm. For purpose of reference, it should be understood that a forearm of a human body may comprise a plurality of muscles. The plurality of muscles are responsible to provide different movements and/or different postures for the wrist and fingers. When an amputee, whose hand is cut in a way that a part of his/her hand muscles is remained, intends to move his/her hand, some of his/her hand muscles may be contracted and/or relaxed according to his/her intention. In an exemplary embodiment, each of the plurality of tags may be embedded into a respective muscle of the plurality of muscles in a way such that when a muscle from the plurality of muscles is contracted and/or relaxed, the respective tag embedded into the muscle thereby moves.

In an exemplary embodiment, the plurality of readers may be configured to sense the plurality of tags movements. The plurality of readers may be associated to a controller that is configured to process the movement signals received from the plurality of tags and accordingly distinguish the amputee's intention for a specific movement and/or posture. In an exemplary embodiment, the controller may further be associated to an artificial hand prosthesis. The controller may also be configured to transmit commands to the artificial hand prosthesis based on the signals received from the plurality of readers in order to control the artificial hand prosthesis movements.

Figure 1B:
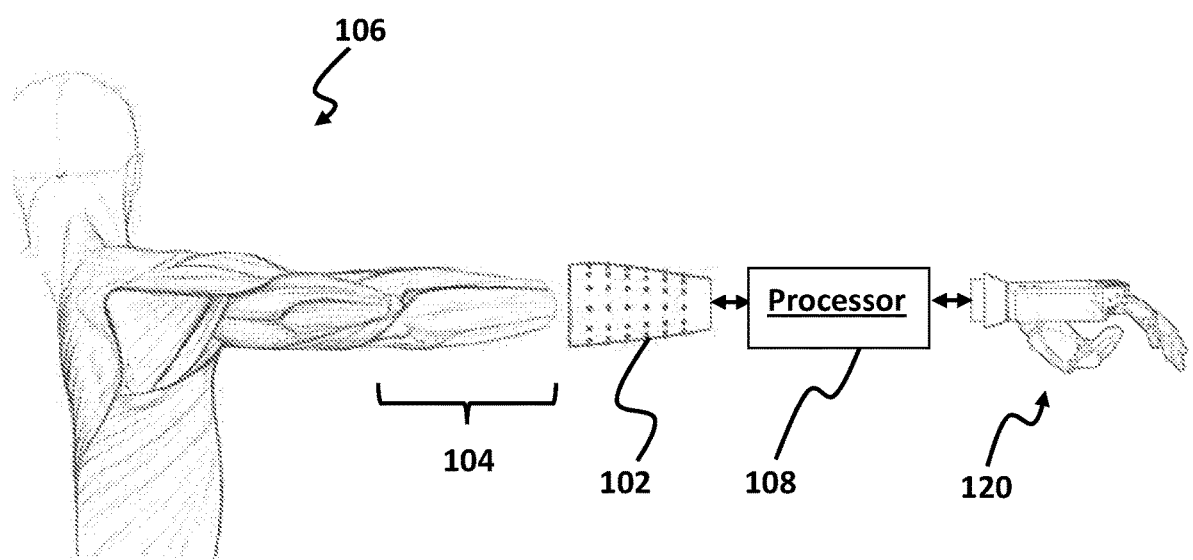
FIG. 1B illustrates an exploded view of a muscle movement detection system worn on a remainder part of an amputated hand, consistent with one or more exemplary embodiments of the present disclosure.
Figure 2:
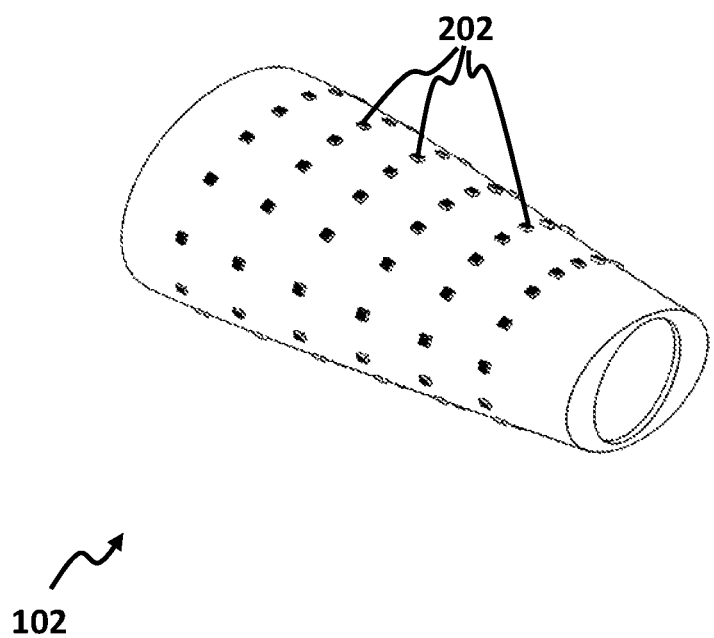
FIG. 2 illustrates a wearable band with a plurality of readers, consistent with one or more exemplary embodiments of the present disclosure.

In order to provide greater clarity regarding the embodiments disclosed herein, additional details are now provided with respect to the drawings. Referring to FIG. 1A and FIG. 1B, an exemplary embodiment of a muscle movement detection system 100 that may be utilized in order to provide some movement commands for an artificial hand prosthesis 120 is depicted. In an exemplary embodiment, muscle movement detection system 100 may comprise a wearable band 102. As shown in FIG. 2, in an exemplary embodiment, wearable band 102 may include a plurality of on-board position readers 202. In an exemplary embodiment, wearable band 102 may be a flexible and stretchable band that may be worn on a remainder part 104 of an amputee's 106 forearm. In some embodiments, wearable band 102 may take the form of an expandable band that may be able to stay in position on remainder part 104 of amputee's 106 forearm. In an alternative embodiment, wearable band 102 may comprise a flat fabric to be wrapped around remainder part 104 of amputee's 106 forearm in order to form a closed loop. Furthermore, in an alternative embodiment, wearable band 102 may be replaced by a socket. For purpose of reference, it should be understood that that a wearable band and a socket may have a substantially similar function in disclosed muscle movement detection system 100.

Figure 3:
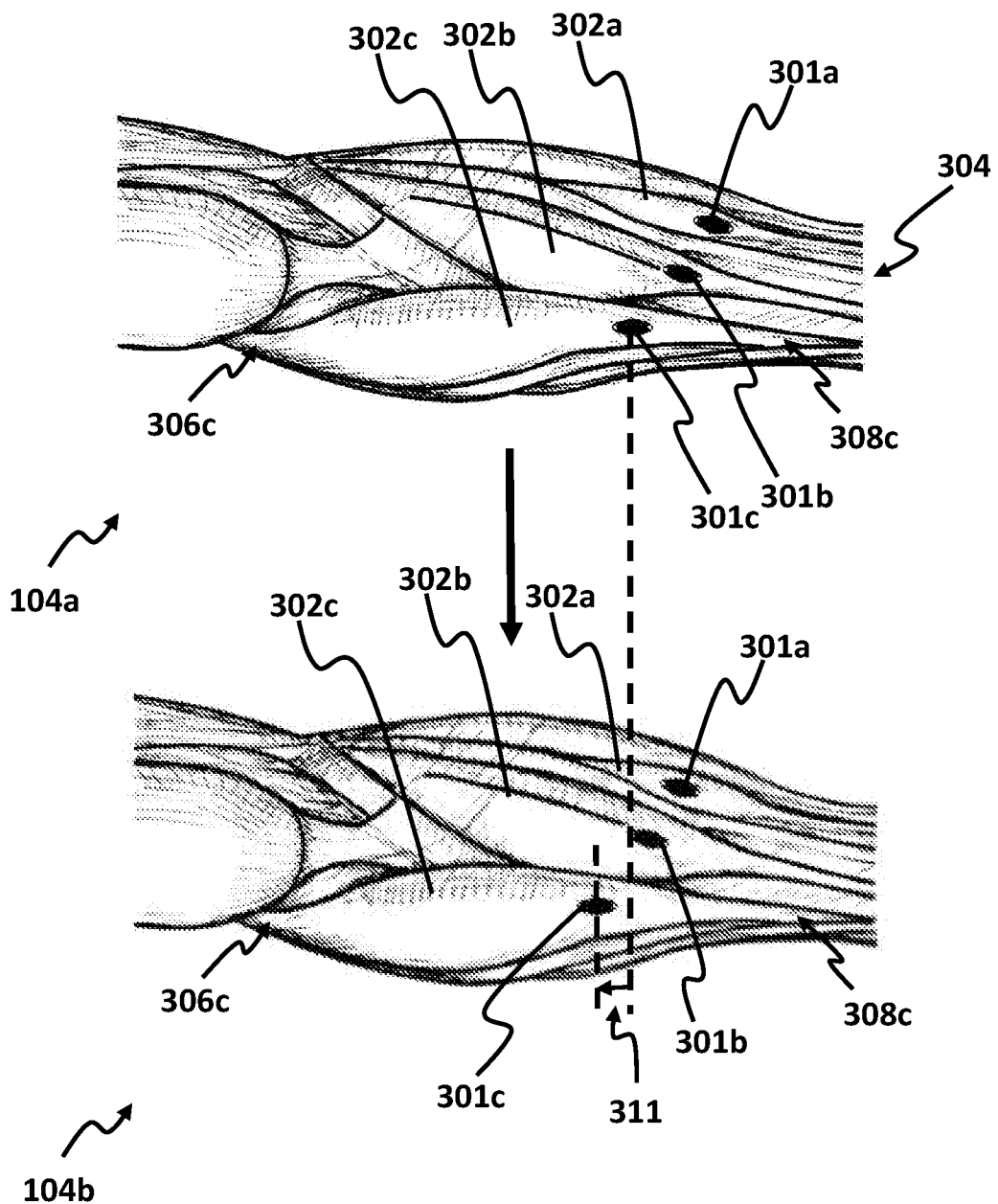
FIG. 3 illustrates a remainder part of an amputated hand including a plurality of muscles with a plurality of passive tags embedded therein, consistent with one or more exemplary embodiments of the present disclosure.

Muscle movement detection system 100 may further include a plurality of passive tags 301 associated with a plurality of forearm muscles 302. In an exemplary embodiment, each passive tag of plurality of passive tags 301 may be embedded or otherwise attached to a respective muscle from plurality of forearm muscles 302. In an exemplary embodiment, as shown in FIG. 3, passive tags 301a, 301b, and 301c may be embedded respectively into forearm muscles 302a, 302b, and 302c. For purpose of reference, it should be understood that a normal forearm of a human body may include a plurality of muscles such as a Brachioradialis muscle, a Flexor Digitorum Profundus muscle, a Flexor Pollicis Longus muscle, a Flexor Digitorum Superficialis muscle, a Palmaris Longus muscle, an Extensor Indicis Proprius muscle, an Extensor Carpi radialis Brevis muscle, an Extensor Carpi radialis Longus muscle, an Extensor digiti minimi muscle, an Extensor carpi ulnaris muscle, and an Anconeus muscle. These muscles are responsible for various hand movements and/or various hand postures. Then, each muscle of plurality of forearm muscles 302, for example forearm muscles 302a, 302b, and 302c, may include one or more of the above-mentioned forearm muscles.

In different embodiments, each passive tag of plurality of passive tags 301, for example, passive tag 301a may be embedded or otherwise attached to different places at a superficial part of respective forearm muscle 302a. In an exemplary embodiment, passive tag 301a may be attached or otherwise embedded into a place close to a distal end 304 of forearm muscle 302a. For purpose of reference, it should be understood that distal end of a forearm muscle may refer to a part of the forearm muscle that is connected to a wrist and proximal end of a forearm muscle may refer to a part of the forearm muscle that is connected to an amputee's elbow. Attaching or otherwise embedding passive tag 301a into a place close to distal end 304 of forearm muscle 302a may provide significant benefits including, but not limited to, increased accuracy of forearm muscle 302a movements detection. In an alternative embodiment, each passive tag of plurality of passive tags 301, for example, passive tag 301a may be embedded or otherwise attached to a respective tendon associated with forearm muscle 302a. In an exemplary embodiment, each of plurality of passive tags 301 may comprise a Radio-frequency identification (RFID) tag coated with a biocompatible silicon or any other biocompatible material. For purpose of reference, it could be understood that utilizing RFID tags may provide significant benefits, including but not limited to, an increase in muscle movement detection precision through embedding different RFID tags associated with different radiofrequency properties. Furthermore, in an alternative embodiment, each of plurality of passive tags 301 may comprise a passive magnetic tag that may be coated with a biocompatible silicon or any other biocompatible material.

With the further reference to FIG. 2, in an exemplary embodiment, plurality of on-board position readers 202 may be attached to an outer surface of wearable band 102. Furthermore, as illustrated in FIG. 2, a subset of plurality of on-board position readers 202 may be arranged circumferentially around wearable band 102. In an exemplary embodiment, plurality of on-board position readers 202 may comprise 30 on-board position readers that may be arranged in a 5 by 6 matrix arrangement. In some embodiments, plurality of on-board position readers 202 may be configured to capture data associated with position. In an exemplary embodiment, plurality of on-board position readers 202 may be configured to capture data associated with plurality of passive tags 301 positions as a function of time. Each passive tag position may include an x-coordinate, a y-coordinate, and a z-coordinate in a predetermined reference coordinate system. For purpose of reference, it may be understood that according to the type of tags, different types of on-board position readers may be used. for example, in different embodiments, each on-board position reader of plurality of on-board position readers 202 may include a magnetic-based reader, an acoustic-based reader, a vibration-based reader, or any other readers capable of detecting the corresponding passive tag position.

For purpose of reference, it should be understood that closeness of plurality of tags to each other may substantially degrade plurality of on-board position readers 202 accuracy. In an exemplary embodiment, in order to increase plurality of on-board position readers 202 accuracy, each passive tag of plurality of passive tags 301 may be embedded into respective forearm muscle from plurality of forearm muscles 302 in a configuration such that a distance between each pair of plurality of passive tags 301 does not exceed 2 centimeters.

In an exemplary embodiment, as shown in FIG. 1B, muscle movement detection system 100 may further include a processor 108. Processor 108 may be configured to receive position data associated with plurality of passive tags 301 positions as a function of time from plurality of on-board position readers 202. Processor 108 may also be configured to detect each forearm muscle contraction and/or relaxation based on changes in associated passive tag position. For purpose of reference, it should be understood that changes in x-coordinate, y-coordinate, and z-coordinate of a passive tag may be indicative of a contraction or relaxation in associated forearm muscle. For example, when forearm muscle 302c is contracted, passive tag 301c may move closer to a proximal end 306c of forearm muscle 302c, whereas, when forearm muscle 302c is relaxed, passive tag 301c may move closer to a distal end 308c of forearm muscle 302c.

FIG. 3 depicts remainder part 104 of amputee's 106 forearm when plurality of forearm muscles 302 are relaxed (designated by 104a) and when plurality of forearm muscles 302 are contracted (designated by 104b). As shown in FIG. 3, when a forearm muscle, for example, forearm muscle 302c of plurality of forearm muscles 302 is contracted, thereby respective passive tag 301c may experience a displacement 311 that may cause passive tag 301c move closer to proximal end 306c of forearm muscle 302c.

In an exemplary embodiment, processor 108 may also be configured to distinguish amputee's 106 intention by detecting plurality of forearm muscles 302 contraction and/or relaxation. In an exemplary embodiment, processor 108 may be in data communication with artificial hand prosthesis 120. Processor 108 may be configured to control artificial hand prosthesis 120 movements based on contraction and/or relaxation of plurality of forearm muscles 302. In an exemplary embodiment, processor 108 may further be configured to transmit commands associated with the finger flexion to artificial hand prosthesis 120 responsive to detection of muscle contraction in the Flexor Digitorum Profundus muscle in an intact hand and/or alternatively in the Flexor Digitorum Profundus muscle and/or the Flexor Digitorum Superficialis muscle in forearm of an amputated person; transmit commands associated with the thumb flexion to artificial hand prosthesis 120 responsive to detection of muscle contraction in the Flexor Pollicis Longus muscle in an intact hand and/or alternatively in the Flexor Pollicis Longus muscle or Flexor Digitorum Superficialis muscle in forearm of an amputated person; transmit commands associated with the thumb opponents to artificial hand prosthesis 120 responsive to detection of muscle contraction in the Oppones Pollicis muscle in an intact hand and/or alternatively Palmaris Longus muscle or Flexor Digitorum Superficialis muscle in forearm of an amputated person; transmit commands associated with the thumb adduction to artificial hand prosthesis 120 responsive to detection of muscle contraction in the Adductor Pollicis Brevis muscle in an intact hand and/or Palmaris Longus muscle or Flexor Digitorum Superficialis muscle in forearm of an amputated person; transmit commands associated with the finger extension to the artificial hand prosthesis 120 responsive to detection of muscle contraction in the Extensor Digitorum muscle in an intact hand and/or alternatively Extensor Digitorum Communis muscle or Extensor Indicis Proper or Extensor Digiti Minimi muscle in forearm of an amputated person; transmit commands associated with the wrist supination to artificial hand prosthesis 120 responsive to detection of muscle contraction in the Biceps Brachii muscle in an intact hand and/or alternatively in any wrist flexor or wrist extensor muscle in forearm of an amputated person, and transmit commands associated with the wrist pronation to artificial hand prosthesis 120 responsive to detection of muscle contraction in the Pronator Teres muscle in an intact hand and/or alternatively any wrist flexor or wrist extensor muscle in forearm of an amputated person.

Figure 4:
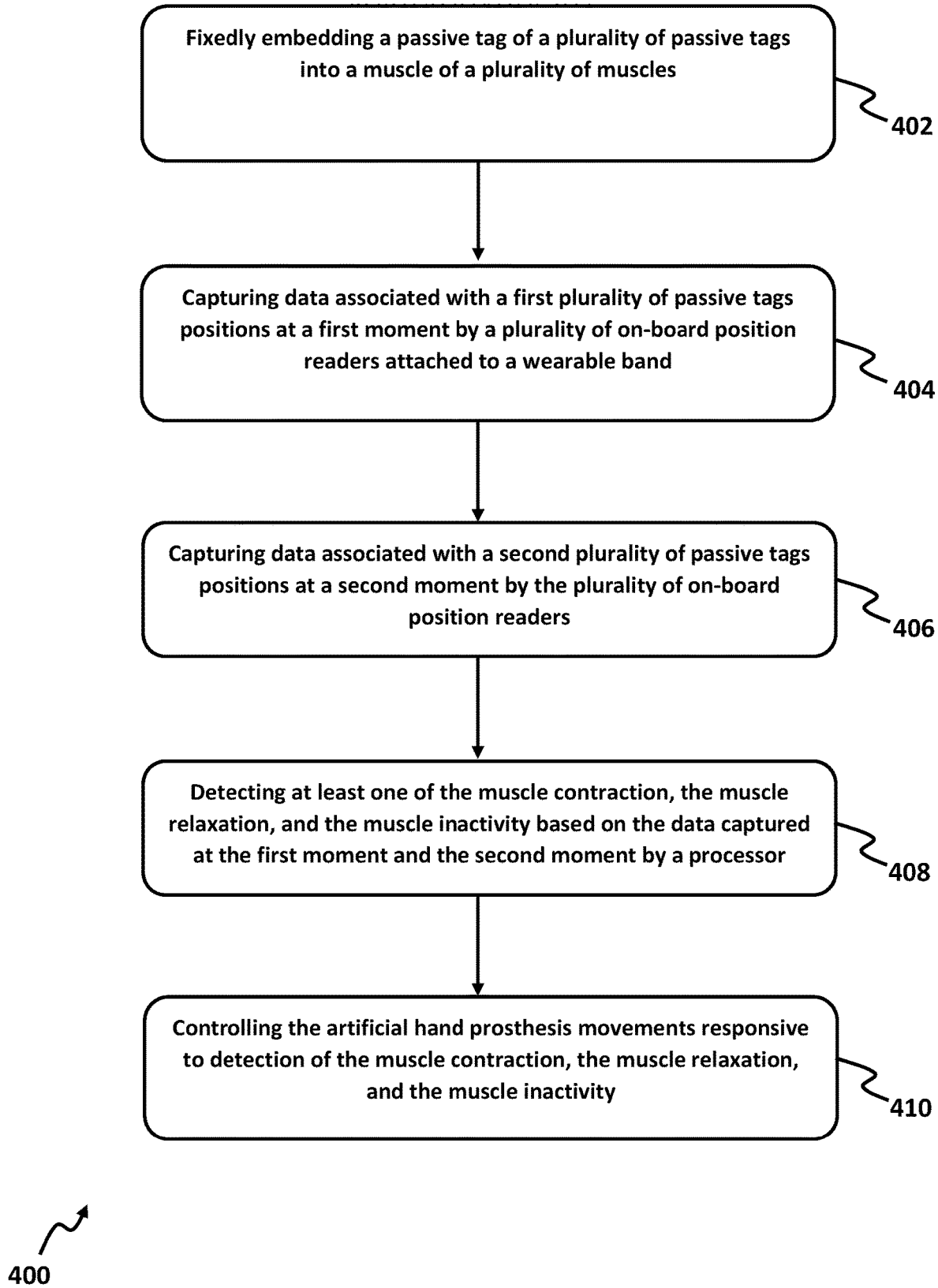
FIG. 4 illustrates a method to detect an amputee's hand muscles movements for controlling an artificial hand prosthesis, consistent with one or more exemplary embodiments of the present disclosure.

Referring now to FIGS. 4, 1A, 1B, 2, and 3, a method 400 to detect an amputee's hand muscles movements for controlling an artificial hand prosthesis is illustrated, consistent with one or more exemplary embodiments of the present disclosure. In some exemplary implementations, method 400 may utilize a wearable band with a plurality of on-board position readers and a plurality of passive tags. As shown in FIG. 4, method 400 may include step 402 of fixedly embedding a passive tag of a plurality of passive tags into a muscle of a plurality of muscles. In an exemplary implementation, method 400 may further include step 404 of capturing data associated with a first plurality of passive tags positions at a first moment by a plurality of on-board position readers attached to a wearable band.

FIG. 1A and FIG. 1B show an exemplary embodiment of a muscle movement detection system 100 that may be utilized in method 400 in order to control artificial hand prosthesis 120. In an exemplary embodiment, the wearable band utilized in method 400 may be substantially similar to wearable band 102. As shown in FIG. 2, in an exemplary embodiment, wearable band 102 may include plurality of on-board position readers 202. In an exemplary embodiment, wearable band 102 may be a flexible and stretchable band that may be worn on remainder part 104 of amputee's 106 forearm. In some embodiments, wearable band 100 may take the form of an expandable band that may be able to stay in position on remainder part 104 of amputee's 106 forearm. In an alternative embodiment, wearable band 102 may comprise a flat fabric to be wrapped around remainder part 104 of amputee's 106 forearm in order to form a closed loop. Furthermore, in an alternative embodiment, wearable band 102 may be replaced by a socket. For purpose of reference, it should be understood that that a wearable band and a socket may have a substantially similar function in disclosed muscle movement detection system 100.

In an exemplary implementation, the plurality of passive tags utilized in method 400 may be substantially similar to plurality of passive tags 301 associated with plurality of forearm muscles 302. In an exemplary embodiment, each passive tag of plurality of passive tags 301 may be embedded or otherwise attached to a respective muscle from plurality of forearm muscles 302. In an exemplary embodiment, as shown in FIG. 3, passive tags 301a, 301b, and 301c may be embedded respectively into forearm muscles 302a, 302b, and 302c. For purpose of reference, it should be understood that a normal forearm of a human body may include a plurality of muscles such as a Brachioradialis muscle, a Flexor Digitorum Profundus muscle, a Flexor Pollicis Longus muscle, a Flexor Digitorum Superficialis muscle, a Palmaris Longus muscle, an Extensor Indicis Proprius muscle, an Extensor Carpi radialis Brevis muscle, an Extensor Carpi radialis Longus muscle, an Extensor digit minimi muscle, an Extensor carpi ulnaris muscle, and an Anconeus muscle. These muscles are responsible for various hand movements and/or various hand postures. Then, each muscle of plurality of forearm muscles 302, for example forearm muscles 302a, 302b, and 302c, may include one or more of the above-mentioned forearm muscles.

In one or more exemplary embodiments, each passive tag of plurality of passive tags 301, for example, passive tag 301a may be embedded or otherwise attached to different places at a superficial part of respective forearm muscle 302a. In an exemplary embodiment, passive tag 301a may be attached or otherwise embedded into a place close to a distal end 304 of forearm muscle 302a. Attaching or otherwise embedding passive tag 301a into a place close to distal end 304 of forearm muscle 302a may provide significant benefits including, but not limited to, increased accuracy of forearm muscle 302a movements detection. In an alternative embodiment, each passive tag of plurality of passive tags 301, for example, passive tag 301a may be embedded or otherwise attached to a respective tendon associated with forearm muscle 302a. In an exemplary embodiment, each of plurality of passive tags 301 may comprise a Radio-frequency identification (RFID) tag coated with a biocompatible silicon material. For purpose of reference, it could be understood that utilizing RFID tags may provide significant benefits, including but not limited to, an increase in muscle movement detection precision through embedding different RFID tags associated with different radiofrequency properties. Furthermore, in an alternative embodiment, each of plurality of passive tags 301 may comprise a passive magnetic tag that may be coated with a biocompatible silicon or any other biocompatible material.

With the further reference to FIG. 2, in an exemplary embodiment, plurality of on-board position readers 202 may be attached to an outer surface of wearable band 102. Furthermore, as illustrated in FIG. 2, a subset of plurality of on-board position readers 202 may be arranged radially around a cross-section of wearable band 102. In an exemplary embodiment, plurality of on-board position readers 202 may comprise 30 on-board position readers that may be arranged in a 5 by 6 matrix arrangement. In some embodiments, plurality of on-board position readers 202 may be configured to capture data associated with position. In an exemplary embodiment, plurality of on-board position readers 202 may be configured to capture data associated with plurality of passive tags 301 positions as a function of time. Each passive tag position may include an x-coordinate, a y-coordinate, and a z-coordinate in a predetermined reference coordinate system. In different embodiments, each on-board position reader of plurality of on-board position readers 202 may include a magnetic-based reader, an acoustic-based reader, a vibration-based reader, or any other readers capable of detecting a passive tag position.

In an exemplary embodiment, in order to increase accuracy of plurality of on-board position readers 202, each passive tag of plurality of passive tags 301 may be embedded into respective forearm muscle of plurality of forearm muscles 302 in a configuration such that a distance between each pair of plurality of passive tags 301 does not exceed 2 centimeters. For purpose of reference, it should be understood that closeness of plurality of tags to each other may substantially degrade plurality of on-board position readers 202 accuracy.

In an exemplary implementation, method 400 may further include step 406 of capturing data associated with a second plurality of passive tags positions at a second moment by plurality of on-board position readers 202. For purpose of reference, it could be understood that in an exemplary implementation, details of step 406 may be analogous to those of step 404 except that step 406 may be carried out at the second moment that may be different from the first moment. In some implementations, method 400 may further include step 408 of detecting at least one of the muscle contraction, the muscle relaxation, and the muscle inactivity based on the data captured at the first moment and the second moment by a processor. In an exemplary implementation, as shown in FIG. 1B, the processor utilized in step 408 of method 400 may be substantially similar to processor 108 of muscle movement detection system 100.

Processor 108 may be configured to receive position data associated to plurality of passive tags 301 positions as a function of time from plurality of on-board position readers 202. Processor 108 may also be configured to detect each forearm muscle contraction and/or relaxation based on changes in associated passive tag position. For purpose of reference, it should be understood that changes in x-coordinate, y-coordinate, and z-coordinate of a passive tag may be indicative of a contraction or relaxation in associated forearm muscle. For example, when forearm muscle 302c is contracted, passive tag 301c may move closer to a proximal end 306c of forearm muscle 302c, whereas when forearm muscle 302c is relaxed, passive tag 301c may move closer to a distal end 308c of forearm muscle 302c.

In an exemplary embodiment, processor 108 may also be configured to distinguish amputee's 106 intention by detecting plurality of forearm muscles 302 contraction and/or relaxation. In an exemplary embodiment, processor 108 may be in data communication with artificial hand prosthesis 120. Processor 108 may be configured to control artificial hand prosthesis 120 movements based on contraction and/or relaxation of plurality of forearm muscles 302.

In an exemplary implementation, method 400 may further include step 410 of controlling the artificial hand prosthesis movements responsive to detection of the muscle contraction, the muscle relaxation, and the muscle inactivity. In an exemplary embodiment, processor 108 may also be configured to distinguish amputee's 106 intention by detecting plurality of forearm muscles 302 contraction and/or relaxation. In an exemplary embodiment, processor 108 may be in data communication with artificial hand prosthesis 120. Processor 108 may be configured to control artificial hand prosthesis 120 movements based on contraction and/or relaxation of plurality of forearm muscles 302. In an exemplary embodiment, the processor may be configured to transmit commands associated with the finger flexion to artificial hand prosthesis 120 responsive to detection of muscle contraction in the Flexor Digitorum Profundus muscle; transmit commands associated with the thumb flexion to artificial hand prosthesis 120 responsive to detection of muscle contraction in the Flexor Pollicis Longus muscle; transmit commands associated with the thumb opponents to the artificial hand prosthesis 120 responsive to detection of muscle contraction in the Flexor Digitorum Superficialis muscle; transmit commands associated with the thumb adduction to artificial hand prosthesis 120 responsive to detection of muscle contraction in the Palmaris Longus muscle; transmit commands associated with the finger extension to artificial hand prosthesis 120 responsive to detection of muscle contraction in the Extensor Digitorum Commonis muscle; transmit commands associated with the wrist supination to artificial hand prosthesis 120 responsive to detection of muscle contraction in the Extensor Carpii Radialis Longus muscle, and transmit commands associated with the wrist pronation to artificial hand prosthesis 120 responsive to detection of muscle contraction in the Extensor Carpi Ulnaris muscle.

Figure 5:
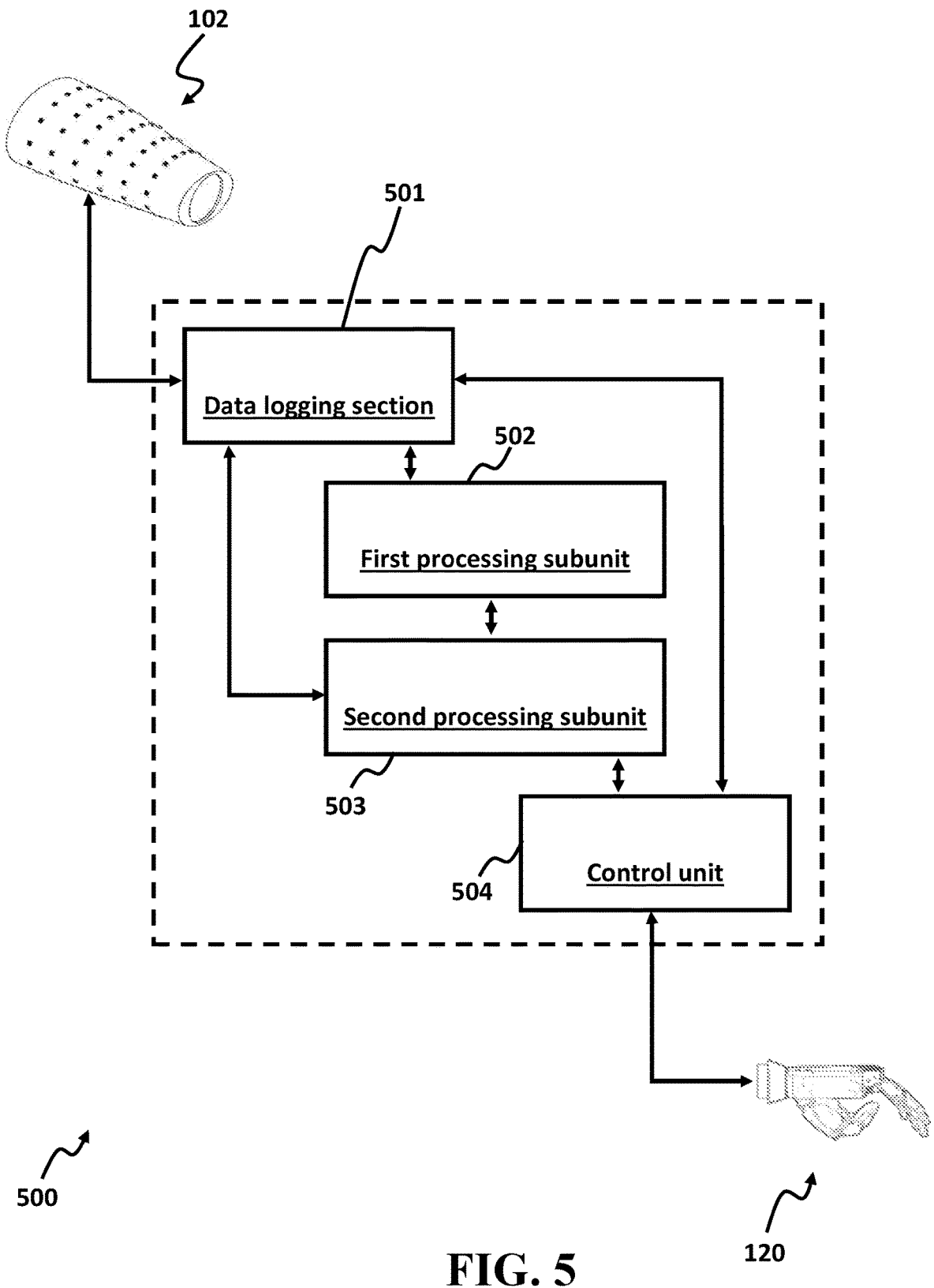
FIG. 5 illustrates a block diagram of an exemplary embodiment of a muscle movement detection system, consistent with one or more exemplary embodiments of the present disclosure.

FIG. 5 illustrates a block diagram of an exemplary embodiment of a muscle movement detection system, directed to detection of muscles movements according to one or more aspects of this disclosure. As shown in FIG. 5, processor 108 may be substantially similar to a processing unit 500. In an exemplary embodiment, processing unit 500 may include a data logging section 501. In an exemplary embodiment, data logging section 501 may be associated with plurality of on-board position readers 202. Data logging section 501 may be connected by wire to plurality of on-board position readers 202 or alternatively, data logging section 501 may contain one or more batteries and a wireless transceiver module for wireless connection to plurality of on-board position readers 202.

In an exemplary embodiment, data logging section 501 may be configured to receive the first plurality of passive tags positions and the second plurality of passive tags positions from plurality of on-board position readers 202 and store the first plurality of passive tags positions and the second plurality of passive tags positions. Alternatively, data logging section 501 may be configured to receive plurality of passive tags 301 positions as a function of time.

As shown in FIG. 5, in an exemplary embodiment, processing unit 500 may further include a first processing subunit 502 that may be associated with data logging section 501. In some embodiments, first processing subunit 502 may be configured to detect at least one of the muscle contraction, the muscle relaxation, and the muscle inactivity by comparing the first plurality of passive tags positions with the second plurality of passive tags positions. Processing unit 500 may further include a second processing subunit 503 associated with first processing subunit 502. Furthermore, second processing subunit 502 may be configured to distinguish amputee's 106 intention based on first processing subunit 502 detections.

In an exemplary embodiment, processing unit 500 may further include a control unit 504 associated with second processing subunit 503. In an exemplary embodiment, control unit 504 may also be associated with artificial hand prosthesis 120. In some embodiments, control unit 504 may be configured to receive amputee's intention from second processing subunit 502 and transmit movement commands to artificial hand prosthesis 120. In an exemplary embodiment, control unit 504 may be connected by wire to artificial hand prosthesis 120 or alternatively, control unit 504 may contain one or more batteries and a wireless transceiver module for wireless connection to artificial hand prosthesis 120.

As described above, processing unit 500 may be configured to continuously detect a muscle contraction and/or relaxation through distinguishing changes in the respective embedded passive tag position and then transmit movement's commands to an artificial hand prosthesis according to the muscle contraction and/or relaxation detection. For purpose of reference, it may be understood that, in an exemplary embodiment, processing unit 500 may be further configured to distinguish extent of the muscle contraction and/or relaxation based on the extent of change in the respective embedded passive tag position. This feature may allow processing unit 500 to transmit movements commands associated with the extent of the contraction and/or relaxation that may be directly correlated with extent of the hand and/or hand prosthesis movement. Furthermore, in some embodiments, processing unit 500 may be configured to distinguish speed of the muscle contraction and/or relaxation based on the speed of change in the respective embedded passive tag position. This feature may allow processing unit 500 to transmit movements commands associated with the speed of the contraction and/or relaxation that may be directly correlated with speed of the hand and/or hand prosthesis movement.

Thus, the exemplary system and method provide an amputee significantly improved precision during movement detection, facilitating the controlling of an artificial prosthesis. As noted above, the exemplary system provides a facility for an amputee, whose hand is cut in a way that a part of his hand muscles is remained. This system is equipped to provide the amputee a substantially exact detection of his/her intention for moving his/her hand. This detection may further be converted to a signal by a processor and then be transmitted to an artificial hand prosthesis to help the artificial hand prosthesis to imitate the movement that the amputee intends to execute.

In exemplary embodiments, exemplary concepts underlying the exemplary system and/or method may be utilized analogously for detecting movements of other organs and muscles in the body. For example, an exemplary system substantially similar to the exemplary embodiments illustrated in the figures may be utilized for detecting movements of a limb associated with an amputated foot and controlling an artificial foot prosthesis. For another example, a system substantially similar to the exemplary embodiments illustrated in the figures may be utilized for detecting movements of a paralytic eyelid based on the other eyelid movements. Likewise, an exemplary system, substantially similar to the exemplary embodiments illustrated in the figures, may be utilized for detecting movements of a paralytic side of diaphragm based on the other intact side movements.

In an exemplary embodiment, an exemplary system and/or exemplary method substantially similar to the exemplary embodiments illustrated in the figures may be utilized for detecting movements of an organ and/or a muscle associated with involunteery movements. For example, an exemplary system may be utilized for detecting involunteery movements of a paralytic part of the bowel based on movements of other intact parts of the bowel.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study, except where specific meanings have otherwise been set forth herein. Relational terms such as "first" and "second" and the like may be used solely to distinguish one entity or action from another without necessarily requiring or implying any actual such relationship or order between such entities or actions. The terms "comprises," "comprising," or any other variation thereof, as used herein and in the appended claims are intended to cover a non-exclusive inclusion, encompassing a process, method, article, or apparatus that comprises a list of elements that does not include only those elements but may include other elements not expressly listed to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is not intended to be used to interpret or limit the scope or meaning of the claims. In addition, in the foregoing Detailed Description, it can be seen that various features are grouped together in various implementations. Such grouping is for purposes of streamlining this disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into this Detailed Description, with each claim standing on its own as a separately claimed subject matter.

While various implementations have been described, the description is intended to be exemplary, rather than limiting and it will be apparent to those of ordinary skill in the art that many more implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A system to detect an amputee's hand muscles movements for controlling an artificial hand prosthesis, the system comprising:
   a plurality of passive tags embedded in a plurality of muscles, a respective passive tag of the plurality of passive tags fixedly embedded into a respective muscle of the plurality of muscles in a configuration that responsive to the respective muscle being contracted or relaxed, the respective passive tag thereby moving;
   a wearable band with a plurality of on-board position readers, the plurality of on-board position readers configured to:
   capture data associated with a first plurality of positions at a first moment, each respective position from the first plurality of positions comprising a position of a respective passive tag from the plurality of passive tags at the first moment; and
   capture data associated with a second plurality of positions at a second moment, each respective position from the second plurality of positions comprising a position of a respective tag from the plurality of passive tags at the second moment; and one or more processors configured to:
   detect at least one of the muscle contraction, the muscle relaxation, and the muscle inactivity based on the data captured at the first moment and the second moment; and
   control the artificial hand prosthesis movements responsive to detection of the muscle contraction, the muscle relaxation, and the muscle inactivity.

2. The system of claim 1, wherein the plurality of passive tags comprise a plurality of RFID tags coated with a biocompatible material.

3. The system of claim 2, wherein the processors are further configured to:
   transmit commands associated with the finger flexion to the artificial hand prosthesis responsive to detection of muscle contraction in at least one of the Flexor Digitorum Profundus muscle and the Flexor Digitorum Superficialis muscle;
   transmit commands associated with the thumb flexion to the artificial hand prosthesis responsive to detection of muscle contraction in at least one of the Flexor Pollicis Longus muscle and the Flexor Digitorum Superficialis muscle;

transmit commands associated with the thumb opponents to the artificial hand prosthesis responsive to detection of muscle contraction in at least one of the Flexor Digitorum Superficialis muscle and the Palmaris Longus muscle;

transmit commands associated with the thumb adduction to the artificial hand prosthesis responsive to detection of muscle contraction in at least one of the Flexor Digitorum Superficialis muscle and the Palmaris Longus muscle;

transmit commands associated with the finger extension to the artificial hand prosthesis responsive to detection of muscle contraction in at least one of the Extensor Indicis Proprius muscle, the Extensor Digitorum Communis muscle, and the Extensor Digiti Minimi Proper muscle;

transmit commands associated with the wrist supination to the artificial hand prosthesis responsive to detection of muscle contraction in at least a muscle from a plurality of wrist flexor and extensor muscles including the Extensor Carpi Radialis Longus muscle and the Extensor Carpi Ulnaris muscle; and transmit commands associated with the wrist pronation to the artificial hand prosthesis responsive to detection of muscle contraction in at least a muscle from a plurality of wrist flexor and extensor muscles including the Extensor Carpi Radialis Longus muscle and the Extensor Carpi Ulnaris muscle.

4. The system of claim 1, wherein a passive tag of the plurality of passive tags is sutured to a superficial part of the muscle close to a skin surface.

5. The system of claim 1, wherein a passive tag of the plurality of passive tags is sutured to a part of the muscle close to a muscle-tendon junction.

6. The system of claim 1, wherein the plurality of passive tags include a first passive tag and a second passive tag, a distance between the first passive tag and the second passive tag larger than 2 centimeters.

7. The system of claim 1, wherein the plurality of on-board position readers comprises 30 on-board position readers arranged in a 5 by 6 matrix arrangement.

8. The system of claim 1, wherein a subset of the plurality of on-board position readers are arranged circumferentially around the wearable band.

9. The system of claim 1, wherein each passive tag position comprises an x-coordinate, a y-coordinate, and a z-coordinate in a predetermined reference coordinate system.

10. The system of claim 9, wherein detecting at least one of a muscle contraction, a muscle relaxation, and a muscle inactivity based on the data captured at the first moment and the second moment comprises:
   comparing the x-coordinate of each passive tag position of the first plurality of passive tags positions with the x-coordinate of the respective passive tag position of the second plurality of passive tags positions;
   comparing the y-coordinate of each passive tag position of the first plurality of passive tags positions with the y-coordinate of the respective passive tag position of the second plurality of passive tags positions; and
   comparing the z-coordinate of each passive tag position of the first plurality of passive tags positions with the z-coordinate of the respective passive tag position of the second plurality of passive tags positions.

11. The system of claim 9, wherein the processors are further configured to:
   detect the muscle contraction responsive to a value of the x-coordinate of the first associated tag position be smaller than a value of the x-coordinate of the second associated tag position;
   detect the muscle relaxation responsive to a value of the x-coordinate of the first associated tag position be larger than a value of the x-coordinate of the second associated tag position; and
   detect the muscle inactivity responsive to a value of the x-coordinate of the first associated tag position be equal to a value of the x-coordinate of the second associated tag position.

12. The system of claim 1, wherein the first moment comprises a moment at which the plurality of muscles are relaxed.

13. The system of claim 1, wherein the plurality of on-board position readers comprise at least one of a magnetic-based reader, an acoustic-based reader, and a vibration-based reader.

14. The system of claim 1, wherein the plurality of muscles comprise a Brachioradialis muscle, a Flexor Digitorum Profundus muscle, a Flexor Pollicis Longus muscle, a Flexor Digitorum Superficialis muscle, a Palmaris Longus muscle, an Extensor Indicis Proprius muscle, an Extensor Carpi radialis brevis muscle, an Extensor Carpi radialis Longus muscle, an Extensor digit minimi muscle, an Extensor carpi ulnaris muscle, and an Anconeus muscle.

15. A method to detect an amputee's hand muscles movements for controlling an artificial hand prosthesis, the method comprising the steps of:
   fixedly embedding a respective passive tag of a plurality of passive tags into a respective muscle of a plurality of muscles, the respective passive tag being moved responsive to the respective muscle being contracted or relaxed;
   capturing data associated with a first plurality of positions at a first moment by a plurality of on-board position readers attached to a wearable band, each respective position from the first plurality of positions comprising a position of a respective passive tag from the plurality of passive tags at the first moment;
   capturing data associated with a second plurality of positions at a second moment by the plurality of on-board position readers, each respective position from the second plurality of positions comprising a position of a respective passive tag from the plurality of passive tags at the second moment;
   detecting at least one of a muscle contraction, a muscle relaxation, and a muscle inactivity based on the data captured at the first moment and the second moment by a processor; and
   controlling the artificial hand prosthesis movements responsive to detection of the muscle contraction, the muscle relaxation, and the muscle inactivity.

16. The method of claim 15, wherein each passive tag position comprises an x-coordinate, a y-coordinate, and a z-coordinate in a predetermined reference coordinate system.

17. The method of claim 15, wherein detecting at least one of the muscle contraction, the muscle relaxation, and the muscle inactivity based on the data captured at the first moment and the second moment comprises:
   comparing the x-coordinate of each passive tag position of the first plurality of passive tags positions with the x-coordinate of the respective passive tag position of the second plurality of passive tags positions;

comparing the y-coordinate of each passive tag position of the first plurality of passive tags positions with the y-coordinate of the respective passive tag position of the second plurality of passive tags positions; and comparing the z-coordinate of each passive tag position of the first plurality of passive tags positions with the z-coordinate of the respective passive tag position of the second plurality of passive tags positions.

18. The method of claim 15, wherein detecting at least one of the muscle contraction, the muscle relaxation, and the muscle inactivity comprises:
  detecting the muscle contraction responsive to a value of the x-coordinate of the first associated tag position be smaller than a value of the x-coordinate of the second associated tag position;
  detecting the muscle relaxation responsive to a value of the x-coordinate of the first associated tag position be larger than a value of the x-coordinate of the second associated tag position; and
  detecting the muscle inactivity responsive to a value of the x-coordinate of the first associated tag position be equal to a value of the x-coordinate of the second associated tag position.

19. The method of claim 15, wherein the plurality of muscles comprise a Brachioradialis muscle, a Flexor Digitorum Profundus muscle, a Flexor Pollicis Longus muscle, a Flexor Digitorum Superficialis muscle, a Palmaris Longus muscle, an Extensor Indicis Proprius muscle, an Extensor Carpi radialis brevis muscle, an Extensor Carpi radialis Longus muscle, an Extensor digit minimi muscle, an Extensor carpi ulnaris muscle, and an Anconeus muscle.

20. The method of claim 15, wherein controlling the artificial hand prosthesis movements comprises:
  transmitting commands associated with the finger flexion to the artificial hand prosthesis responsive to detection of muscle contraction in at least one of the Flexor Digitorum Profundus muscle and the Flexor Digitorum Superficialis muscle;
  transmitting commands associated with the thumb flexion to the artificial hand prosthesis responsive to detection of muscle contraction in at least one of the Flexor Pollicis Longus muscle and the Flexor Digitorum Superficialis muscle;
  transmitting commands associated with the thumb opponents to the artificial hand prosthesis responsive to detection of muscle contraction in at least one of the Flexor Digitorum Superficialis muscle and the Palmaris Longus muscle;
  transmitting commands associated with the thumb adduction to the artificial hand prosthesis responsive to detection of muscle contraction in at least one of the Flexor Digitorum Superficialis muscle and the Palmaris Longus muscle;
  transmitting commands associated with the finger extension to the artificial hand prosthesis responsive to detection of muscle contraction in at least one of the Extensor Indicis Proprius muscle, the Extensor Digitorum Communis muscle, and the Extensor Digiti Minimi Proper muscle;
  transmitting commands associated with the wrist supination to the artificial hand prosthesis responsive to detection of muscle contraction in at least a muscle from a plurality of wrist flexor and extensor muscles including the Extensor Carpii Radialis Longus muscle and the Extensor Carpi Ulnaris muscle; and
  transmitting commands associated with the wrist pronation to the artificial hand prosthesis responsive to detection of muscle contraction in at least a muscle from a plurality of wrist flexor and extensor muscles including the Extensor Carpii Radialis Longus muscle and the Extensor Carpi Ulnaris muscle.

* * * * *